(12) United States Patent
Middleman et al.

(10) Patent No.: US 6,351,658 B1
(45) Date of Patent: Feb. 26, 2002

(54) MULTIPLE-CODE OXIMETER CALIBRATION ELEMENT

(75) Inventors: Lee Middleman, Portola Valley; Paul D. Mannheimer, Danville; Michael J. Bernstein, San Ramon; Michael E. Fein, Mountain View, all of CA (US)

(73) Assignee: Mallinckrodt, Inc., Hazelwood, MO (US)

( * ) Notice: Subject to any disclaimer, the term of this patent is extended or adjusted under 35 U.S.C. 154(b) by 0 days.

(21) Appl. No.: 09/407,015

(22) Filed: Sep. 28, 1999

Related U.S. Application Data
(60) Provisional application No. 60/102,315, filed on Sep. 29, 1998.

(51) Int. Cl.[7] .................................................. A61B 5/00
(52) U.S. Cl. ........................ 600/331; 600/322; 600/323
(58) Field of Search .................. 600/309–311, 322–324, 600/326, 328, 331, 476, 473; 356/39–42

(56) References Cited

U.S. PATENT DOCUMENTS

| | | | |
|---|---|---|---|
| 3,720,199 A | | 3/1973 | Rishton et al. |
| 3,790,910 A | | 2/1974 | McCormack ............ 235/151.3 |
| 4,258,251 A | | 3/1981 | Donaldson .................... 235/92 |
| 4,303,984 A | | 12/1981 | Houvig ........................ 364/571 |
| 4,570,160 A | * | 2/1986 | Imazeki et al. ................ 345/34 |
| 4,621,643 A | | 11/1986 | New, Jr. et al. |
| 4,684,245 A | | 8/1987 | Goldring ...................... 356/41 |
| 4,700,708 A | | 10/1987 | New, Jr. et al. |
| 4,942,877 A | | 7/1990 | Sakai et al. |
| B14,446,715 | | 9/1991 | Bailey .............................. 73/1 |
| 5,246,003 A | | 9/1993 | DeLonzor |
| 5,259,381 A | | 11/1993 | Cheung et al. |
| 5,429,129 A | * | 7/1995 | Lovejoy et al. ............. 600/310 |
| 5,645,059 A | | 7/1997 | Fein et al. |
| 5,654,712 A | * | 8/1997 | Cheng .......................... 341/155 |
| 5,722,403 A | * | 3/1998 | McGee et al. ............... 600/373 |
| 5,779,630 A | * | 7/1998 | Fein et al. .................... 600/323 |
| 5,830,129 A | * | 11/1998 | Baer et al. ................... 600/300 |
| 5,987,343 A | * | 11/1999 | Kinast .......................... 600/323 |
| 5,818,985 A | * | 2/2000 | Merchant et al. ............. 385/20 |

FOREIGN PATENT DOCUMENTS

| | | | |
|---|---|---|---|
| EP | 0 638 872 A1 | 2/1995 | .......... G06K/19/07 |
| EP | 0 640 978 A2 | 3/1995 | ............ G11C/7/00 |
| EP | 0 671 675 A2 | 9/1995 | ......... G05B/19/042 |
| WO | WO 95/16387 | 6/1995 | ............ A61B/5/00 |
| WO | WO 96/41138 | 12/1996 | ............ G01J/3/10 |
| WO | WO 97/22294 | 6/1997 | ............ A61B/5/00 |

\* cited by examiner

*Primary Examiner*—Eric F. Winakur
*Assistant Examiner*—Matthew Kremer
(74) *Attorney, Agent, or Firm*—Townsend and Townsend and Crew LLP (57) ABSTRACT

An encoding element which is backward compatible and will provide a single coded value to older analyzers in response to first signal, but will also provide a second coded value to a new analyzer or monitor. In one embodiment, both coded values are provided over the same first and second leads which are compatible with existing sensors. In another embodiment, a first voltage level produces a first current from the encoding element, while a second voltage level will produce the second coded value. In another embodiment, a first coded value is provided in response to a DC current from older analyzers. A second coded value is provided in response to a AC signal from newer analyzers. Yet another embodiment provides the coded value in the form of a resonant circuit in the AC driven mode. In another embodiment, the first coded value is provided over the same two leads after a period of time, with the second value being provided prior to that period of time passing.

43 Claims, 6 Drawing Sheets

MULTIPLE-CODE OXIMETER CALIBRATION ELEMENT

CROSS-REFERENCE TO RELATED APPLICATIONS

This application claims priority from U.S. Provisional Application Ser. No. 60/102,315, filed Sep. 29, 1998 which is incorporated herein by reference in its entirety for all purposes.

BACKGROUND OF THE INVENTION

The present invention relates to oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

An encoding mechanism is shown in U.S. Pat. No. 4,700,708, the disclosure of which is incorporated herein by reference. This mechanism relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary, a coding resistor is placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe.

U.S. Pat. No. 5,259,381 recognizes that the coded value of the wavelength of the red LED provided by a coding resistor may be inaccurate, since the actual wavelength can vary with temperature. Accordingly, this patent teaches including a temperature sensor in the oximeter probe to measure the actual temperature. With the actual temperature, and the coded wavelength value, a look-up table can be consulted to determine the actual LED wavelength for that temperature.

Another method of storing coded information regarding the characteristics of the LEDs is shown in U.S. Pat. No. 4,942,877. This patent discloses using an EPROM memory to store digital information, which can be provided in parallel or serially from the sensor probe to the remote oximeter.

Other examples of coding probe characteristics exist in other areas. Multiple calibration values are sometimes required, with this making the circuitry more complex or requiring many leads. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another probe with digital characterization information stored in a PROM, which is read serially using a shift register.

Typically, the coding element is mounted in the probe itself. For instance, U.S. Pat. No. 4,621,643 shows the coding resistor mounted in the probe element itself. In addition, U.S. Pat. No. 5,246,003 shows the coding resistor being formed with a printed conductive material on the probe itself.

In some devices, an electrical connector coupled by a cable to a device attached to a patient may include a coding element. For example, U.S. Pat. No. 3,720,199 shows an intra-aortic balloon catheter with a connector between the catheter and a console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

In some applications, it would be desirable to provide multiple independent codes for different values using only two leads. This may allow backward compatibility, or compatibility with probes of other manufacturers. For example, Nellcor Puritan Bennett produces a probe with an encoded calibration resistor for providing a signal indicative of a known wavelength of a red LED, which signal upon being read by an oximeter allows the oximeter to select appropriate calibration coefficients for use in calculating arterial oxygen saturation. In order to modify such a Nellcor-type sensor to provide multiple independent codes, one approach is to use a different range of resistors to indicate a different characteristic. For example, Ohmeda Systems is believed to use a first range of resistors for their reusable sensors, and a second range of resistors for the disposable sensors. Thus, a single resistor essentially encodes in its most significant bit the sensor type, and then indicates the calibration curve to be used with the least significant bits of its value. Marquette is believed to produce a sensor and monitor which uses the presence of a resistance to indicate the type of sensor, with no resistance being present indicating a Marquette sensor. Other sensors are believed to read multiple values using three pins.

U.S. Pat. No. 5,645,059 teaches using a modulated signal to provide the coded data to a remote analyzer. U.S. Pat. No. 5,429,129 shows using a voltage regulator to produce a specific voltage value in response to an attempt to read by the analyzer.

SUMMARY OF THE INVENTION

The present invention provides an encoding element which is backward compatible and will provide a single coded value to older analyzers in response to a first signal, but will also provide a second coded value to a new analyzer or monitor. Both coded values are provided over the same first and second leads which are compatible with existing probes or sensors. The encoding element can be a resistor or other discrete component, a hybrid, a component group, an integrated circuit, or any other encoding mechanism.

In one embodiment, a first voltage level produces a first current from the encoding element, while a second voltage level will produce the second coded value. In one version of this embodiment, a zener diode is activated to connect a second resistance or to simply bypass a resistor when a high level voltage is provided exceeding the zener value. When the lower voltage is provided, the analyzer sees only the resistance it expects for the older type of sensor.

In a second embodiment, a first coded value is provided in response to a DC current from older analyzers. A second coded value is provided in response to an AC signal from newer analyzers. Yet another embodiment provides the coded value in the form of a resonant circuit in the AC driven mode. By varying the frequency applied, the frequency resulting in the highest voltage, indicating the resonant frequency, can be found. Thus, the coded value is provided in the value of the resonant frequency chosen.

In another embodiment, the second coded value is provided over the same two leads after a period of time, with the first value being provided prior to that period of time passing. If the period of time is chosen to correspond with that used by older analyzers, backward compatibility is ensured. In one embodiment, a thermistor is used which will heat up as current is applied over time, and eventually switch in a second coding resistor.

In yet another embodiment, a first coded value is provided in response to a DC current from older analyzers, and a second code is provided in response to an input digital code from newer analyzers over the same two leads.

In one embodiment, since some older analyzers may drive the calibration resistor with different polarities, the new coding element is compatible to provide the desired value regardless of the polarity of the driving signal to determine the first coded value.

In one embodiment, a third lead is used which is not used in prior art oximeters. Many prior art oximeters had positions for two additional pins which were not used. By using one of these pins, a control signal can be sent to switch which encoded value is provided across the original 2 leads. Alternately, three encoded values can be provided over the 3 leads.

For a fuller understanding of the nature and advantages of the invention, reference should be made to the following description taken in conjunction with accompanying drawings.

DETAILED DESCRIPTION OF THE INVENTION

Figure 1A:
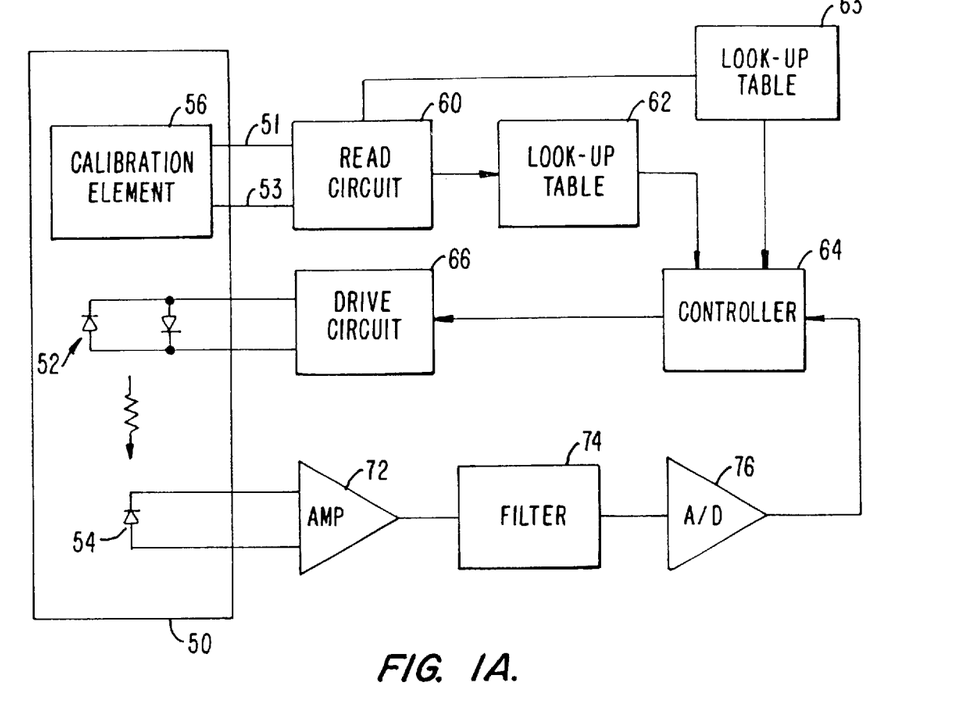
FIG. 1A is a block diagram of an oximeter system which would incorporate the present invention.

FIG. 1A is a block diagram of a pulse oximeter system incorporating a calibration element 56 according to the invention. The calibration element is part of the sensor 50 which also includes red and infrared LEDs 52 as in the prior art, along with a detector 54.

A read circuit 60 is provided for reading multiple coded values across the two leads 51, 53 connected to calibration element 56. One value is provided to a look-up table 62 to determine appropriate wavelength dependent coefficients for the oxygen saturation calculation, as in the prior art. The other value(s) are then provided to another look up table(s) 63 which provides input (e.g., coefficients) to other calculations performed by controller 64. These additional calculations may enhance the performance and/or safety of the system.

Controller 64 provides signals to a drive circuit 66, to control the amount of drive current provided to LEDs 52.

As in the prior art, detector 54 is connected through an amplifier 72 and a filter 74 to an A/D converter 76. This forms a feedback path used by controller 64 to adjust the drive current to optimize the intensity range of the signal received. For proper operation the signal must be within the analog range of the circuits employed. The signal should also be well within the range of A/D converter 76 (e.g., one rule that may be applied is to adjust LED drives and amplifier gains so that both red and IR signals fall between 40% and 80% of full scale reading of converter 76). This requires correct and independent settings for both the red and infrared LEDs. The current invention allows for another feedback path which may alter the LED settings based on other sensor characteristics contained in the coding of the calibration element.

Figure 1B:
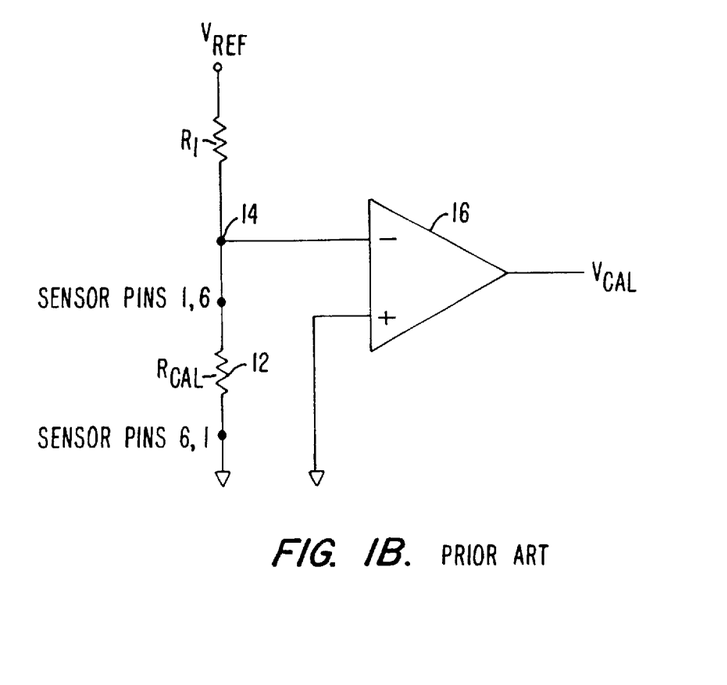
FIG. 1B is a diagram of a prior art read circuit for reading a simple Rcal coding resistor.

FIG. 1B illustrates a prior art reader circuit in existing analyzers. It is desirable to have a coding element according to the present invention be readable by such a prior art circuit. An Rcal resistor 12 in a prior art sensor is connected between pins 1 and 6 of a probe. The read circuit connects either pin 1 or 6 to ground, and the other pin to a node 14. Node 14 is connected through a resistor R1 to a voltage source Vref. Node 14 is also connected to the negative input of an operational amplifier 16. The positive input of amplifier 16 is connected to ground. A voltage divider circuit is thus created by the Rcal and R1 resistors, with the created voltage being applied to the negative input of amplifier 16. The output of amplifier 16 is an analog voltage Vcal, which corresponds to the value of Rcal. Vcal is then applied to a D-A converter (not shown) to provide a value which can be used to index into a table of coefficients such as look-up table 62 of FIG. 1A. The values of Vref and R1 may vary from monitor to monitor, and the polarity across Rcal may vary. Although this polarity is not an issue for a simple Rcal resistor, is an issue for a new circuit being placed in parallel with Rcal and designed to be backward compatible.

Figure 3A:
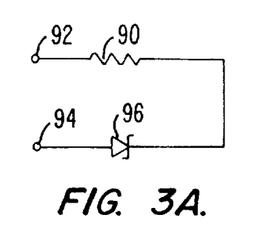
FIGS. 3A–3F illustrate embodiments of circuit implementations which would respond to two levels of voltage as illustrated in FIG. 2A.
Figure 3B:
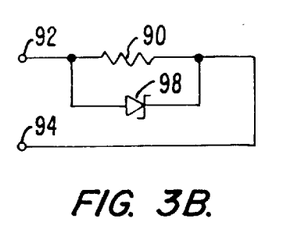
Figure 3C:
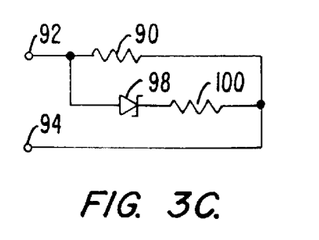

FIGS. 3A–3F illustrate some embodiments of circuits implementing a coding system for two or more independent values using zener diodes. As shown in FIG. 3A, a calibration resistor 90 as in the prior art is provided between two leads 92 and 94. However, a zener diode 96 is also added. FIG. 3B shows a variant in which zener diode 98 is placed in parallel with resistor 90 rather than in series. In the embodiment of FIG. 3C, a second resistor 100 is added in series with zener diode 98. The zener diode is an example of a "non-linear" element, which is an element which produces a signal which does not linearly correspond to a measuring signal applied to the element.

Figure 2A:
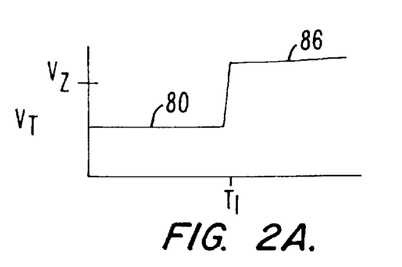
FIG. 2A is a graphical illustration of two voltage levels selecting different coded values.

For circuits of the type shown in FIG. 3C, one possible reading process would be as shown in FIG. 2A. For applied positive voltages 80 between pins 94, 92 which are below the zener 98 voltage $V_z$, the current would be that expected from resistor 90. For applied voltages 86 above the zener voltage $V_z$, the current would depend on both resistor 90 and resistor 100. By measuring the current at both voltage 80 below the zener voltage and voltage 86 above the zener voltage, and also knowing the voltage $V_z$ of Zener 98, the values of both resistors 90 and 100 can be calculated. By testing at many voltages, the zener voltage $V_z$ can be determined. So if the designer chooses, the zener voltage $V_z$ can be used to define a $3^{rd}$ independent value. Similar methods to those described above can easily be used to drive the circuit types shown in FIGS. 3A through 3E to derive the various zener voltages and resistances employed in these circuits. For example, in FIG. 3A, various positive voltages below and above $V_z$ can be applied between pins 92, 94 to determine $V_z$ and the resistance of resistor 90. In FIG. 3B, various positive voltages both below and above $V_z$ can be applied between pins 94, 92 to determine $V_z$ and the resistance of resistor 90.

Figure 3D:
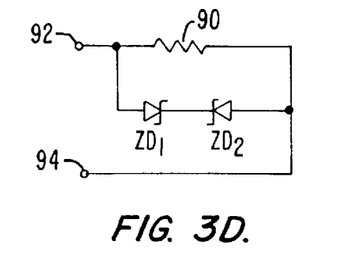
Figure 3E:
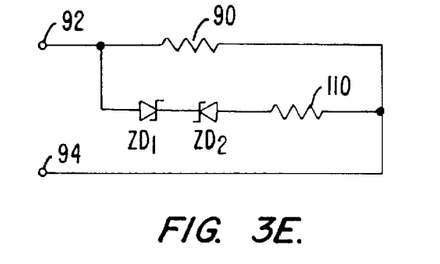

FIGS. 3D and 3E show back to back zeners of opposite polarity. These circuits are similar to those of FIGS. 3B and 3C, except that they are designed to be backward compatible and thus work with older oximeters which are designed to read only one coded value encoded in a circuit resistance as taught in U.S. Pat. No. 4,621,643 or as shown in FIG. 1B. Some such older oximeters may drive lead 92 with the positive polarity, while others might drive lead 94 positive. In FIG. 3D, two back to back zener diodes $ZD_1$ and $ZD_2$ are used. In FIG. 3E, back to back zener diodes $ZD_1$ and $ZD_2$ are used along with a second resistor 110. The response of these circuits can be made identical regardless of the polarity of voltage drive applied. For example, if $ZD_1$ is the same as $ZD_2$, any polarity voltage between pins 92, 94 which is below $V_z$ will create a current which will reveal the resistance of resistor 90 for both circuits shown in FIGS. 3D and 3E. Any polarity voltage above $V_z$ will create a current which will indicate the parallel resistance of resistors 90, 110 in FIG. 3E. The zener voltage will be determinable in both these circuits by applying incrementally higher voltages across pins 92, 94 until a parallel resistance is detected, as in the circuit of FIG. 3C.

Figure 2B:
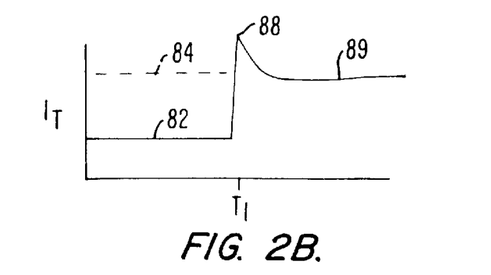
FIG. 2B is a graphical illustration of the use of current transient information to facilitate reading of two different coded values.
Figure 3F:
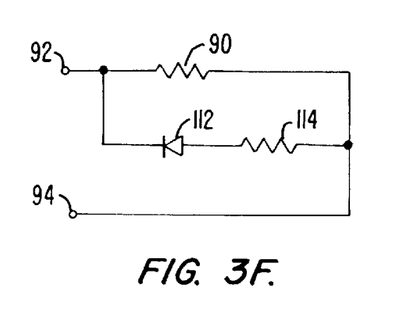
Figure 3G:
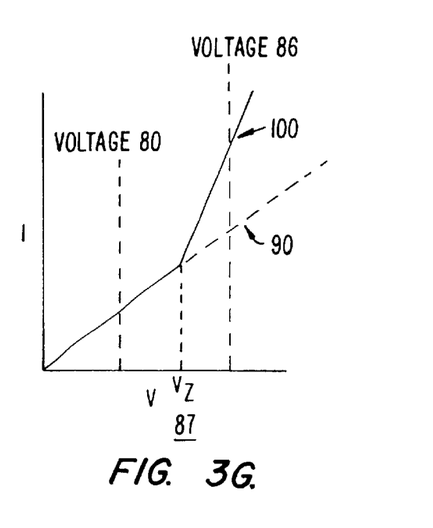
FIG. 3G is a graph illustrating the operation of the circuit of FIG. 3C or 3E.
Figure 4A:
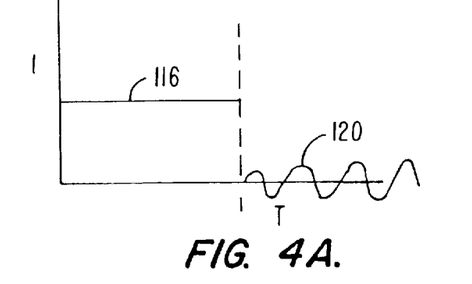
FIGS. 4A–4C are graphical representations of two coded values being provided in response to DC and time-dependent voltages.
Figure 4B:
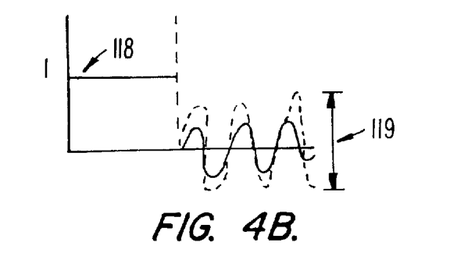
Figure 5A:
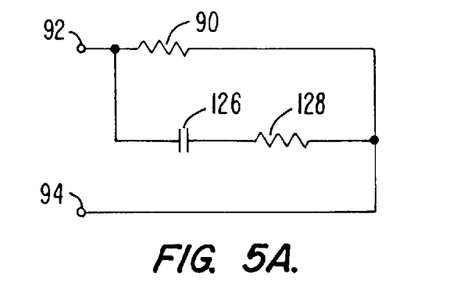
FIGS. 5A–5E are embodiments of circuit implementations which would respond to the voltages shown in FIG. 4.
Figure 5B:
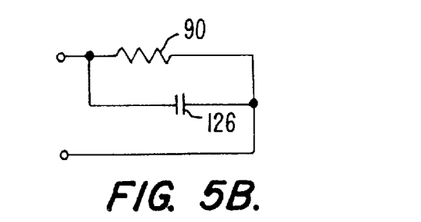

FIG. 3F shows an embodiment which will work with a known polarity for prior oximeters. A diode 112 prevents a resistor 114 from being seen when the diode is reversed biased. Thus, the resistance seen will be resistor 90. When the diode is forward biased, the total resistance will be resistor 90 and resistor 114 in parallel, given a new coded value. This embodiment has the advantage that it does not require supply voltages greater than $V_z$. FIGS. 2A and 2B illustrate the operation of the reading of a calibration element according to the circuit shown in FIG. 5A, which uses a capacitor 126 to allow separate reading of resistors 90 and 128. When a first voltage level 80 is applied for some time, it will produce current level 82 corresponding to calibration resistor 90 in the same manner as when using prior art sensors and prior art monitors. Current level 82 would be one of multiple current levels 84 depending on the resistance value of resistor 90. To detect a secondary value, at time T1 the voltage would be suddenly changed to a second voltage 86. This higher voltage 86 could be provided by new monitors or analyzers. Immediately after the change in voltage, the current peak 88 would depend on the values of both resistor 90 and resistor 128. As capacitor 126 charged up to the new voltage, the current would decay to level 89, representative of the value of resistor 90 and the new voltage. So by comparing the values of current peak 88 and current 89, the value of resistor 128 could be calculated. Alternatively, both values could be calculated by comparing the responses of this network to DC and AC excitation as shown in FIGS. 4A and 4B. FIG. 4A illustrates the application of DC voltage 116 during one time interval and AC voltage 120 during another time interval. FIG. 4B illustrates the responding currents 118 (DC) and 119 (AC). During the period of DC operation, the value of resistor 90 would be determined as in the prior art. Current 118 would depend only on the value of resistor 90. The response of the network to the AC signal 120 would be different, as the AC signal causes current to flow through resistor 128 and capacitor 126 as well as resistor 90 making the total current greater than the DC case. For different values of resistor 128, there would be different values of AC current 119, allowing the value of resistor 128 to be calculated to decode the second value. Optionally, the resistor 128 could be omitted, as in FIG. 5B, and the value of capacitor 126 and resistor 90 determined in response to the DC and AC inputs illustrated in FIG. 4A.

Figure 5C:
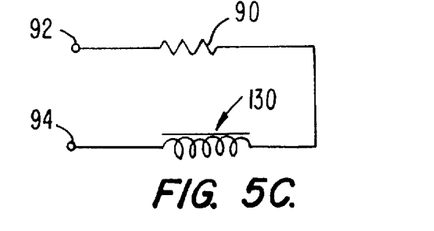

In FIG. 5C, an inductance 130 is placed in series with resistor 90. The inductor is essentially invisible to a DC voltage, but will provide an impedance to an AC voltage, giving a different impedance value, and thus a different code, when an AC excitation such as that shown in FIG. 4A is applied.

Figure 4C:
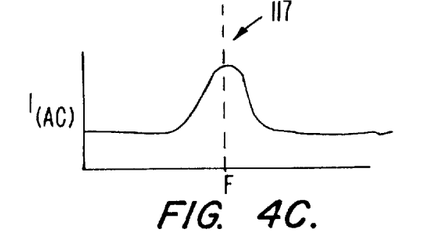
Figure 5D:
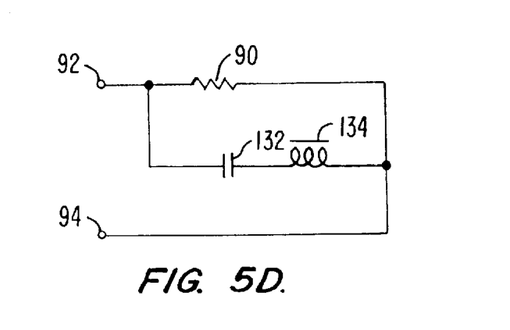
Figure 5E:
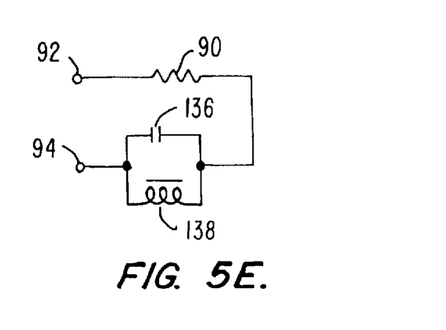

FIGS. 5D and 5E add a resonant circuit. In FIG. 5D capacitor 132 and inductor 134 form a series resonator. FIG. 5E shows a parallel resonant circuit with capacitor 136 and inductor 138. A resonant circuit would operate a little bit differently from the method shown in FIG. 4A. The DC resistance would be determined as in the prior art, to determine a first encoded value. The second value would be encoded by the resonant frequency. Different codes could be assigned to different resonant frequencies to provide the second encoded value. The resonant frequency can be found by sweeping the frequency of the test signal over the expected range. During this sweep, the response of the calibration element would either peak upward or downward at the resonant frequency, depending on whether a parallel or series resonator was employed. Such a response is illustrated by resonance peak 117 in FIG. 4C. The resonant frequency can also be determined from the impulse response of the calibration element.

Figure 6:
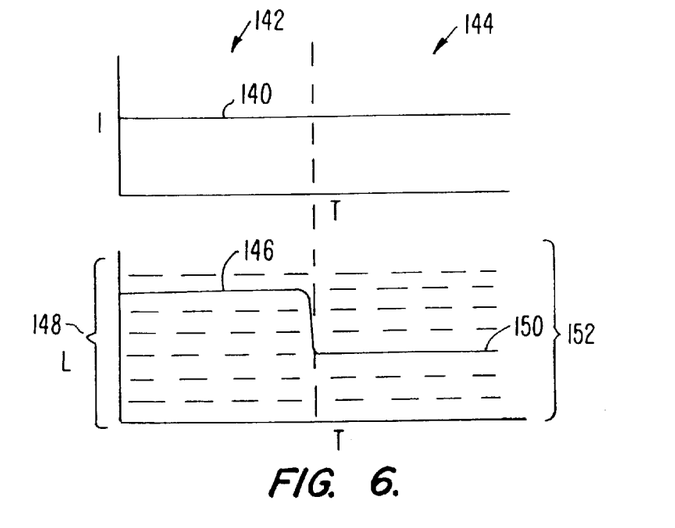
FIG. 6 is a graphical representation of selecting different coded values based on the time of application of a current.

FIG. 6 shows yet another encoding approach using time to distinguish between first and second codes. As shown, a constant current 140 is applied both for a time period 142 and subsequent time period 144. In such an approach older oximeters, which apply power to the calibration network continuously, would sample and measure the coded value within time period 144 which represents the response after a long time has passed. New oximeters would either measure during time period 142 upon initial power up, or switch the power off for a period (long enough, for example, for thermistor 154 of FIG. 7 to cool off) before the measurement. This allows a particular voltage value 146 out of a number of possible values 148 to be chosen in time period 142. In time period 144, a particular voltage 150 may result out of a number of possible voltage values 152.

Figure 7:
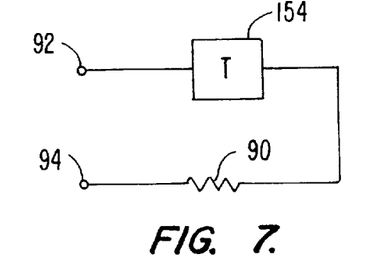
FIG. 7 is a diagram of one embodiment of a circuit implementing the system of FIG. 6.

An example of a circuit implementing the method of FIG. 6 is shown in FIG. 7. An NTC (negative temperature coefficient) thermistor 154 is connected in series with resistor 90. Initially, the circuit will have a resistance equal to the sum of the resistance of resistor 90 and the cold resistance of thermistor 154. After running a current through thermistor 154 for a period of time, it becomes sufficiently heated that its resistance drops significantly, giving a different coded value. This can be designed so that the sum of the hot resistance of thermistor 154 and the resistance of resistor 90 represents exactly the old code under the prior art. Other obvious variations are possible, such as having resistor 90 connected in parallel with resistor 156, or using PTC (positive temperature coefficient) thermistors.

Figure 13:
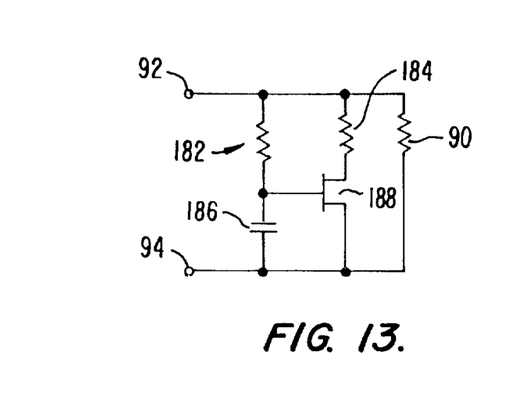
FIG. 13 is a circuit diagram of another circuit for selecting different coded values based on the time of application of a current.

FIG. 13 shows an alternate type of time dependent circuit. In this circuit, when voltage is initially applied, capacitor 186 is not charged and current flows only through resistors 90 and 182. As voltage continues to be applied, capacitor 186 will eventually charge up above the gate threshold voltage of FET 188. At this time the FET turns on, connecting resistor 184 into the circuit. The current will then increase, allowing a second value to be decoded.

Figure 8:
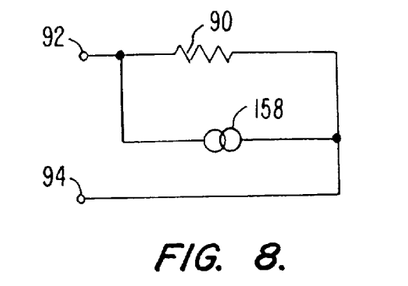
FIG. 8 is a circuit diagram of an embodiment using a current source to produce the second coded value.
Figure 9:
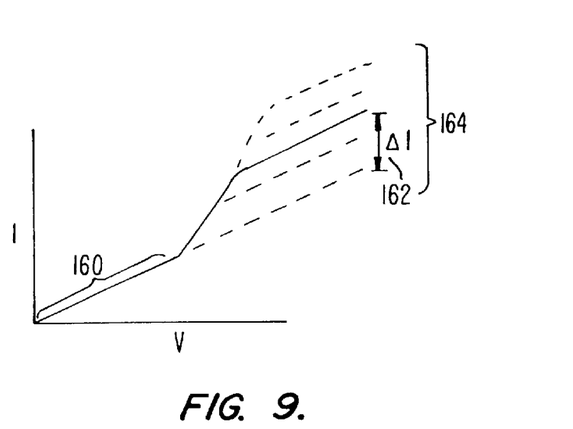
FIG. 9 is a graph illustrating the operation of a circuit as in FIG. 8.

FIG. 8 shows another embodiment in which a current regulator 158 is added in parallel to resistor 90. FIG. 9 illustrates the resulting current versus applied voltage. In a first region 160 of the current/voltage curve, as current is increased, the voltage will increase linearly across resistor 90. This range can be used to read the encoded value of resistor 90 using old oximeters to supply a fixed current into either pin 92 or 94. By providing a voltage high enough to activate the constant current regulator 158, an incremental current 162 is added by the current regulator 158, so the total current now becomes the current expected from resistor 90 at that voltage plus the fixed current of current regulator 158. By determining the amount of current change which occurs above the activation, the second encoded value can be obtained. The second encoded value, used by newer oximeters, thus encodes the value in the maximum current. By using different current regulator designs, different possible maximum current values 164 can be used to encode different values.

Figure 10:
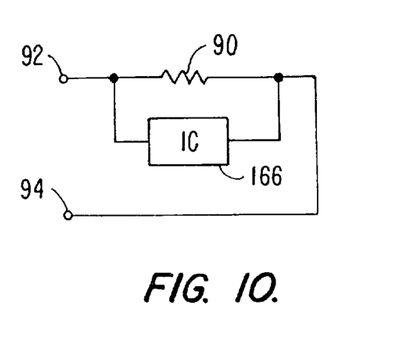
FIG. 10 is a circuit diagram of an embodiment using an IC to provide a coded value for the second encoded value.

FIG. 10 shows another embodiment in which an integrated circuit (IC) 166 is placed in parallel with resistor 90. IC 166 can be made to have almost any desired response. One example is to make the IC non-responsive to a standard voltage for reading resistor 90 in older oximeters. However, when the voltage is switched on and off in a sequence representing a particular digital code, it can trigger a response from IC 166, which may be an output code of its own or some other response. In addition, an IC can be made to mimic any of the analog circuit responses described in this document. IC 66 may contain digital circuits, analog circuits, or a combination thereof.

Figure 11:
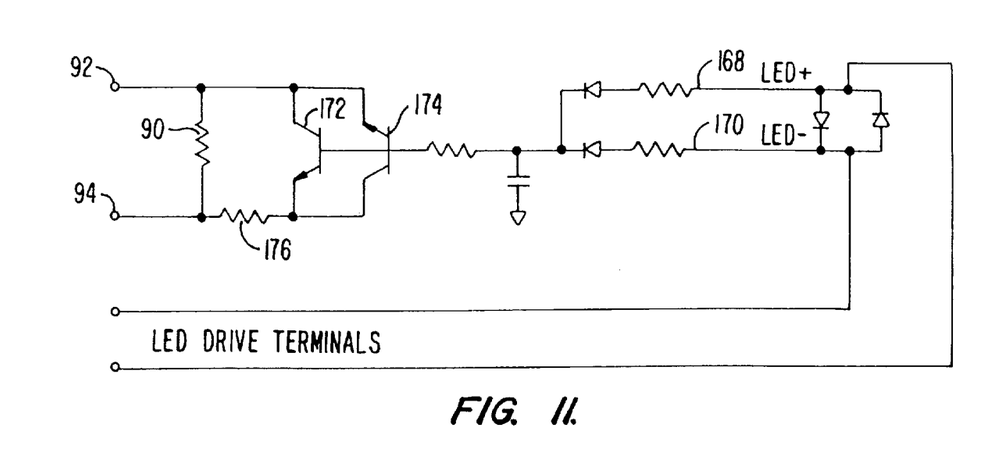
FIG. 11 is a diagram of a circuit implementing a state machine approach to provide a second coded value over the same two leads used for interconnecting a first encoding element.

FIG. 11 shows yet another embodiment in which the value of resistor 90 is read when it is measured without pulsing the LEDs in the oximeter probe (i.e. LED drive lines 168 and 170 are both at high impedance, so that no signals are applied to turn on either transistor 172 or transistor 174). Once the LEDs are pulsed, the LED drive signals, at both the positive and negative end, are applied to leads 168 and 170. These pulses will alternatively activate transistors 172 and 174 such that a second resistor 176 is placed in parallel with resistor 90 when the LEDs are being driven with pulse signal. Thus, two coded values are provided by providing the second coded values at a different time, when the LED pulse drive signals are applied. This system might also be expanded to provide different secondary values when the red and IR LEDs are pulsed.

Figure 12A:
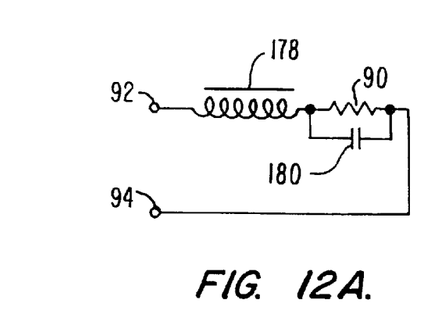
FIGS. 12A and 12B are a circuit and layout diagram of an embodiment in which two coded values are provided by the real and imaginary parts of a complex impedance.
Figure 12B:
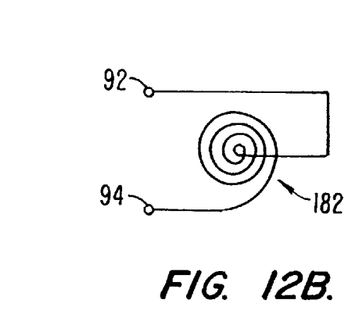

FIG. 12A and 12B illustrate an embodiment in which the two encoded values are provided as a real impedance value, represented by resistor 90, and an imaginary impedance value, provided by inductor 178 in series and capacitor 180 in parallel. A physical embodiment of the circuit shown schematically in FIG. 12A could be provided by a coil 182 as shown in FIG. 12B, with the coil providing all three impedance elements. Inductance 178 would be provided in straightforward fashion by the coil's windings. Capacitance 180 would be provided by capacitive coupling between the coils of the windings, and resistance 90 would be provided by the resistance of the windings.

The embodiments described above have each comprised two leads connected to an encoding element. Alternate embodiments further comprise a third lead connected to that encoding element, with the advantage that the third lead may reduce the cost or complexity of providing back-compatible encoding elements which furnish additional information when utilized with new instruments. In addition, some prior art sensors do not use all the pins of the connectors, with certain pins being reserved. Accordingly, backward compatibility can be achieved by utilizing one of those reserved pins as a third lead for an encoding element in a new sensor. The prior art oximeter monitors will not use the third lead, and accordingly backward compatibility is achieved. Such embodiments are illustrated by FIGS. 14 and 15.

Figure 14:
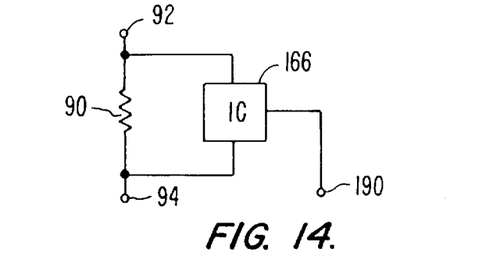
FIGS. 14 and 15 are circuit diagrams of 3 lead embodiments.
Figure 15:
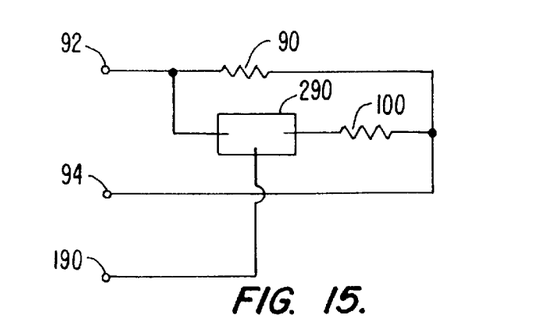

FIG. 14 shows an encoding element similar to the device of FIG. 10, in which read resistor 90 is in parallel with integrated circuit (IC) 166 between leads 92 and 94. In the embodiment of FIG. 14, IC 166 is designed to present a much higher terminal impedance than resistor 90, so long as no voltage is connected to added lead 190. In old instruments, lead 190 would have no connection to the instrument, and the encoding element would appear simply as resistor 90. New instruments would provide a connection to lead 190, and from time to time would apply an enabling voltage to lead 190, causing IC 166 to emit a series of pulses revealing the encoded information stored in IC 166. The advantage of the FIG. 14 embodiment over that of FIG. 10 is that the new instruments would not be required to have high-voltage power supplies, capable of emitting a large control voltage. In the FIG. 10 embodiment, on the other hand, the voltage required to switch on the functioning of IC 166 would have to be larger than any voltage normally applied to leads 92 and 94 by older instruments, in order that ICC 166 would not be turned on by any old instrument.

The same philosophy illustrated by FIG. 14 may also be applied in the various analog circuit configurations. As one example, FIG. 15 shows a device similar to the encoding element of FIG. 3C. FET switch 290 is designed to prevent very high impedance if no voltage is applied to lead 190, and to be switchable by new instruments into a low impedance state by application of an appropriate voltage to lead 190. Thus, old instruments would see only resistor 90, while new instruments would see the combined effects of resistors 90 and 100, or 90 alone, depending on the voltage applied to lead 190.

Figure 16:
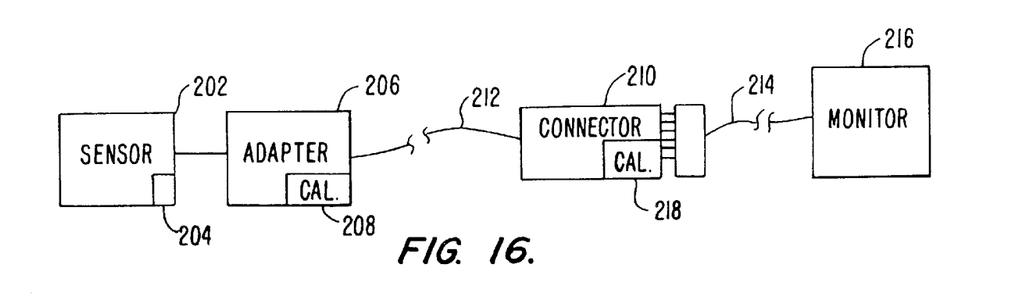
FIG. 16 is a diagram illustrating encoder locations in a sensor, adapter or connector.

FIG. 16 is a diagram illustrating different positions for locating an encoding or calibration element according to the present invention. FIG. 16 shows a sensor 202 with an encoding element 204. The sensor can be connected to an adapter 206, and alternately an encoding element 208 could be included in adapter 206. A connector 210 is shown connecting cable 212 to another cable 214, which is connected to a monitor 216. In yet another alternate embodiment, an encoding element 218 can be included in connector 210. In alternate embodiments, the two encoded values may be produced from two different locations. For example, the encoding element of the prior art could be element 204 in sensor 202, while a second encoded value could be provided from an encoding element 208 or 218.

Figure 17:
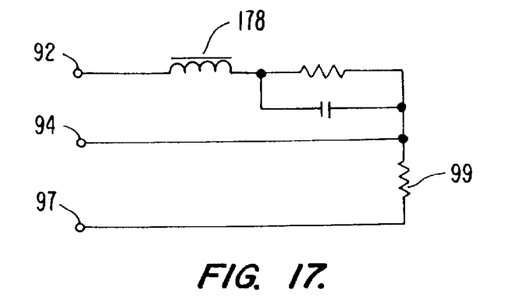
FIG. 17 is a diagram illustrating a 3-lead embodiment modification of FIG. 12A.

As will be understood by those skilled in the art, the present invention may be embodied in other specific forms without departing from the essential characteristics thereof. For example, alternate three-pin embodiments could be provided by connecting a resistance to a third pin at one side, and at the other side to any position along the circuits of FIGS. 3–10 or 12A, for example. An example is shown in FIG. 17 with a three-pin and extra resistor embodiment corresponding to a modified FIG. 12A. As can be seen, an additional pin 97 and resistor 99 are added. Accordingly, the foregoing description is intended to be illustrative, but not limiting, of the scope of the invention which is set forth in the following claims.

What is claimed is:

1. An oximeter probe encoding apparatus, comprising:
    first and second leads; and
    an encoding device configured to produce a first code value at said first and second leads in response to a first signal applied by an oximeter monitor to said first and second leads, said encoding device being configured to produce a second code value at said first and second leads in response to a second signal applied by said oximeter monitor to said first and second leads.

2. The apparatus of claim 1 wherein at least three code values are produced.

3. The apparatus of claim 1 further comprising a third lead, wherein said second code value is produced in response to a control signal on said third lead.

4. The apparatus of claim 1 wherein said first code value is produced when said leads are driven with a first signal, and said second code value is produced when said leads are driven with a second signal.

5. The apparatus of claim 4 wherein said encoding device comprises a single encoding element.

6. The apparatus of claim 4 wherein said encoding device comprises:
    a first encoding element, coupled to said first and second leads, configured to produce the first code value at said first and second leads when said first and second leads are driven with the first signal; and
    a second encoding element, coupled to said first and second leads, configured to produce the second code value at said first and second leads, when said first and second leads are driven with the second signal.

7. The apparatus of claim 6 wherein said first encoding element is a passive element, and said second encoding element is an active element.

8. The apparatus of claim 6 wherein:
    said first encoding element comprises a resistor; and
    said second encoding element comprises a non-linear element.

9. The apparatus of claim 8 wherein said non-linear element comprises a first zener diode.

10. The apparatus of claim 9 wherein said zener diode is in series with said resistor.

11. The apparatus of claim 9 wherein said zener diode is in parallel with said resistor.

12. The apparatus of claim 9 wherein said second encoding element further comprises:
    a second resistor in series with said zener diode.

13. The apparatus of claim 9 wherein said second element further comprises:
    a second zener diode in series with said first mentioned zener diode, and having an opposite configuration to said first mentioned zener diode.

14. The apparatus of claim 13 wherein said second element further comprises a second resistor in series with said zener diodes.

15. The apparatus of claim 6 wherein:
    said first encoding element comprises a first resistor; and
    said second encoding element comprises a diode in parallel with said first resistor, and a second resistor in series with said diode.

16. The apparatus of claim 6 wherein:
    said first element comprises a resistor; and
    said second element comprises a current source coupled to said resistor.

17. The apparatus of claim 6 wherein said second encoding element comprises an AC impedance.

18. The apparatus of claim 6 wherein said first signal is a DC signal, and the second signal varies with time.

19. The apparatus of claim 18 wherein:
    said first encoding element comprises a resistor; and
    said second encoding element comprises a capacitor in parallel with said resistor.

20. The apparatus of claim 19 further comprising a second resistor in series with said capacitor.

21. The apparatus of claim 19 wherein:
    said first encoding element comprises a resistor; and
    said second encoding element comprises an inductor.

22. The apparatus of claim 18 wherein:
    said first encoding element comprises a resistor; and
    said second encoding element comprises an arrangement of components forming a resonant circuit.

23. The apparatus of claim 18 wherein:
    said first encoding element comprises a resistor; and
    said second encoding element comprises a parallel arrangement of an inductor and a capacitor in series with said resistor.

24. The apparatus of claim 18 wherein:
    said first encoding element comprises a resistor; and said second encoding element comprises a series arrangement of an inductor and a capacitor in parallel with said resistor.

25. The apparatus of claim 18 wherein:

said encoding device comprises a single component with capacitance, inductance and resistance.

26. The apparatus of claim 4 wherein said first signal varies in a first manner with time and the second signal varies in a second, different manner with time.

27. The apparatus of claim 4 wherein said first and second code values are produced independent of a polarity of said first and second drive signals.

28. The apparatus of claim 27 wherein one of said first and second signals consists essentially of a constant current.

29. The apparatus of claim 1 wherein said encoding device comprises an integrated circuit configured to be activated to provide said second code value in response to the second signal.

30. The apparatus of claim 29 wherein at least three code values are produced.

31. The apparatus of claim 29 wherein said first and second code values are produced independent of a polarity of said first and second drive signals.

32. The apparatus of claim 1 wherein said encoding device is an integrated circuit, said first code value corresponds to a value from a resistor across said first and second leads, and said second code value is a digital code.

33. The apparatus of claim 1 wherein said apparatus is mounted at least partially in an adapter for an oximeter sensor.

34. The apparatus of claim 1 wherein said apparatus is mounted at least partially in a connecting cable of an oximeter sensor.

35. The apparatus of claim 1 wherein said apparatus is part of an oximeter sensor.

36. An oximeter probe encoding apparatus, comprising:

first and second leads;

a first encoding device comprising a resistor configured to produce a first code value in response to a first signal at a first time; and a second encoding device configured to produce a second code value at a second time in response to said first signal, said second encoding device comprising a thermistor arranged to switch between first and second resistive states after being heated by being provided a current for a period of time.

37. An oximeter probe encoding apparatus, comprising:

first and second leads;

an encoding device configured to produce a first code value at said first and second leads in response to an oximeter monitor applying a first signal to said first and second leads at a first time; and a capacitor coupled to said encoding device, wherein a charge on said capacitor changes in response to said oximeter monitor applying the first signal to said first and second leads, causing said encoding device to produce a second code value at said first and second leads at a second time.

38. An oximeter probe encoding apparatus, comprising:

first and second leads; and a plurality of encoding devices configured to produce a plurality of code values at said first and second leads in response to signals applied by an oximeter monitor to said first and second leads.

39. An oximeter sensor encoding apparatus, comprising:

first and second leads;

a first encoding element coupled to said first and second leads, configured to produce a first code value at said first and second leads when said first and second leads are driven with a DC signal provided by an oximeter monitor; and a second encoding element, coupled to said first encoding element, configured to produce a second code value at said first and second leads when said first and second leads are driven with an AC signal provided by said oximeter monitor;

wherein said first and second encoding elements are configured to produce the same first code value regardless of the polarity of said DC signal.

40. An oximeter sensor encoding apparatus, comprising:

first and second leads;

a first encoding element coupled to said first and second leads, configured to produce a first code value at said first and second leads when driven with a first voltage or current level applied by an oximeter monitor to said first and second leads at a first time; and a second encoding element, coupled to said first encoding element, configured to produce a second code value at said first and second leads when driven with a second voltage or current level applied by said oximeter monitor to said first and second leads at a second time;

wherein said first and second encoding elements are configured to produce the same first code value regardless of the polarity of said first voltage or current level.

41. An oximeter sensor encoding apparatus, comprising:

first and second leads;

a first encoding device configured to provide a first encoded value across said first and second leads in response to a first signal applied by an oximeter monitor to said first and second leads; and a second encoding device configured to provide a second encoded value across said first and second leads in response to a control signal on a third lead from said oximeter monitor.

42. An oximeter probe encoding apparatus, comprising:

a first lead;

a second lead;

a third lead;

an encoding device configured to produce a first code value at said first and second leads in response to a first signal applied by an oximeter monitor to said first and second leads, said encoding device being configured to produce a second code value at said first and second leads in response to a second signal from said oximeter monitor, and said encoding device being configured to produce a third code value at said first and second leads.

43. An oximeter probe encoding apparatus, comprising:

an LED driven by a drive current;

first and second leads;

a first encoding element coupled to said first and second leads, configured to produce a first code value at said first and second leads when driven with a first voltage or current level applied by an oximeter monitor to said first and second leads at a first time; and a second encoding element configured to produce a second code value at said first and second leads when driven with a second voltage or current level provided by said LED drive current at a second time.

* * * * *